US00PP16563P3

(12) United States Plant Patent
Chahbandar

(10) Patent No.: US PP16,563 P3
(45) Date of Patent: May 23, 2006

(54) ARTICHOKE PLANT NAMED 'BCA 3-21'

(50) Latin Name: *Cynara scolymus* L.
Varietal Denomination: BCA 3-21

(76) Inventor: Medhat Chahbandar, Domaine la Quintane, Torreilles (FR), 66440

( * ) Notice: Subject to any disclaimer, the term of this patent is extended or adjusted under 35 U.S.C. 154(b) by 42 days.

(21) Appl. No.: 10/372,050

(22) Filed: Feb. 20, 2003

(65) Prior Publication Data

US 2004/0168242 P1 Aug. 26, 2004

(51) Int. Cl.
*A01H 5/00* (2006.01)

(52) U.S. Cl. ..... Plt./258
(58) Field of Classification Search ..... Plt./258
See application file for complete search history.

(56) References Cited

U.S. PATENT DOCUMENTS

PP12,206 P2 11/2001 Colfer
PP12,208 P2 11/2001 Colfer
PP14,578 P2 * 3/2004 Colfer ..... Plt./258 .....

* cited by examiner

*Primary Examiner*—Kent Bell
*Assistant Examiner*—W. C. Haas
(74) *Attorney, Agent, or Firm*—Townsend and Townsend and Crew LLP

(57) ABSTRACT

A new and distinct cultivar of Artichoke plant named 'BCA 3-21' characterized by more compact shape than its parent, Camus. It has more daughter plants and shoots than Camus. Its bract coloration is distinctive with a violet or purple tip on a light green base.

4 Drawing Sheets

Botanical designation: *Cynara scolymus* L.
Variety denomination: 'BCA 3-21'.

BACKGROUND OF THE INVENTION

The present invention comprises a new and distinct cultivar of artichoke plant, botanically known as *Cynara scolyms* L., and herein referred to by the cultivar name 'BCA 3-21'. This new variety is characterized by a distinctive violet bract tip, a greater number of shoots and daughter plants than the parent and other artichoke varieties known to the inventor, a more compact shape than the parent with a distinctive flavor.

*Cynara scolymus* L., commonly known as Globe artichoke, is a perennial herb and is a member of the family Asteraceae, also known as the Compositae family. Globe artichokes comprise: leaves, which are pinnately lobed, but primarily spineless; globose capitula composed of overlapping layers of large involucral bracts; and receptacles, which are enlarged and fleshy. Globe artichoke plants are essentially grown for the production of the immature flower heads (or buds). The immature buds are harvested before the appearance of sexual organs (or the mature flower) and are considered vegetable delicacies. Fresh artichokes may be steamed, boiled, or baked after which the fleshy receptacle, inner and outer bracts, and parts of the floral stem may be eaten.

The new cultivar is a product of a planned breeding program carried out by the inventor near Perpignan, France. It originated as a single plant, which was obtained from a cross between two "Camus" (unpatented) artichokes. It was noticeably different than its parents in the color and shape of the bracts and the overall shape in the fruit head. The inventor performed asexual reproduction of a single plant of the new cultivar via division. It was demonstrated that the combination of characteristics as herein disclosed for the new cultivar are firmly fixed and retained through successive generations of asexual reproduction.

BRIEF SUMMARY OF THE INVENTION

The following traits have been repeatedly observed and are determined to be basic characteristics of 'BCA 3-21'. These traits in combination distinguish the artichoke as a new and distinct cultivar. 'BCA 3-21' is distinguished from the parent by a distinctive violet bract tip over a light green base (at a certain point of maturation), a greater number of shoots and daughter plants than the parent, and a more compact shape (the fruit head) than the parent with a new, distinctive flavor.

'BCA 3-21' has not been observed under all possible environmental conditions. The phenotype of the new cultivar may vary with variations in environment such as temperature, humidity, light intensity and day length, without any change in the genotype. However, the following observations, measurements and values, except for seed observations, describe the new cultivar as grown in Lompoc, Calif. under conditions which closely approximate those generally used in horticultural practice.

Lompoc is located on California's central coast in Santa Barbara County. Conditions can vary in the summer months. Air temperatures can range between the low 60's to 80's. The relative humidity is generally high. Prevailing winds are northwesterly and rainfall averages 12 inches per year.

In the following description, holding quality was measured by the physical appearance of the head. This includes the head's appearance following 3 and 7 day storage periods in cold storage at 34° F. The head's exterior (oxidation) was observed at each of the two observation points. Browning and blackening of plant tissue was evaluated as light, moderate and extreme. Overall storage response was measured by observing heads following 3 and 7 day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, necrotic or chlorotic lesions or any abiotic responses to environmental conditions.

BRIEF DESCRIPTION OF THE DRAWINGS

This new variety is illustrated by the accompanying photographic drawings. The colors in the photograph are as true to those of the plant as can be reasonably obtained from conventional photographic procedures.

DETAILED DESCRIPTION OF THE INVENTION

Figure 1:
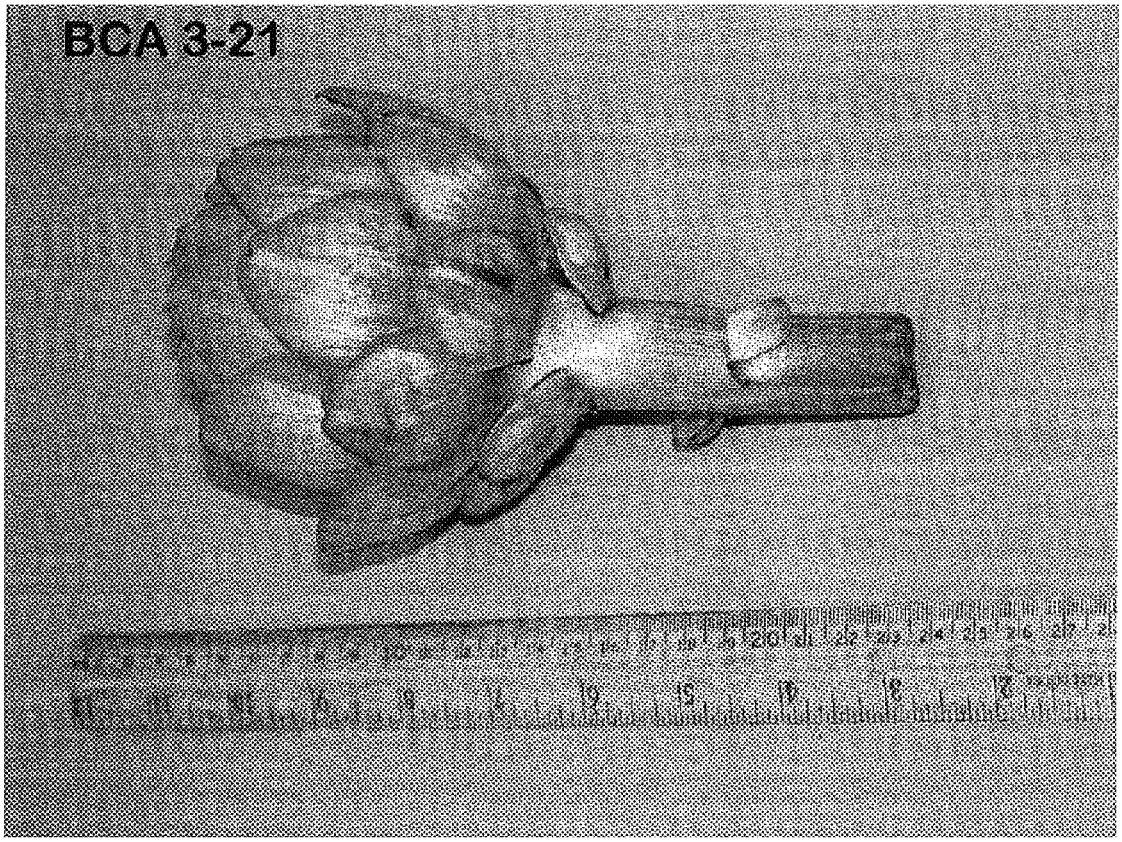
FIG. 1 shows a side elevational view of 'BCA 3-21's' fruit in full color.
Figure 2:
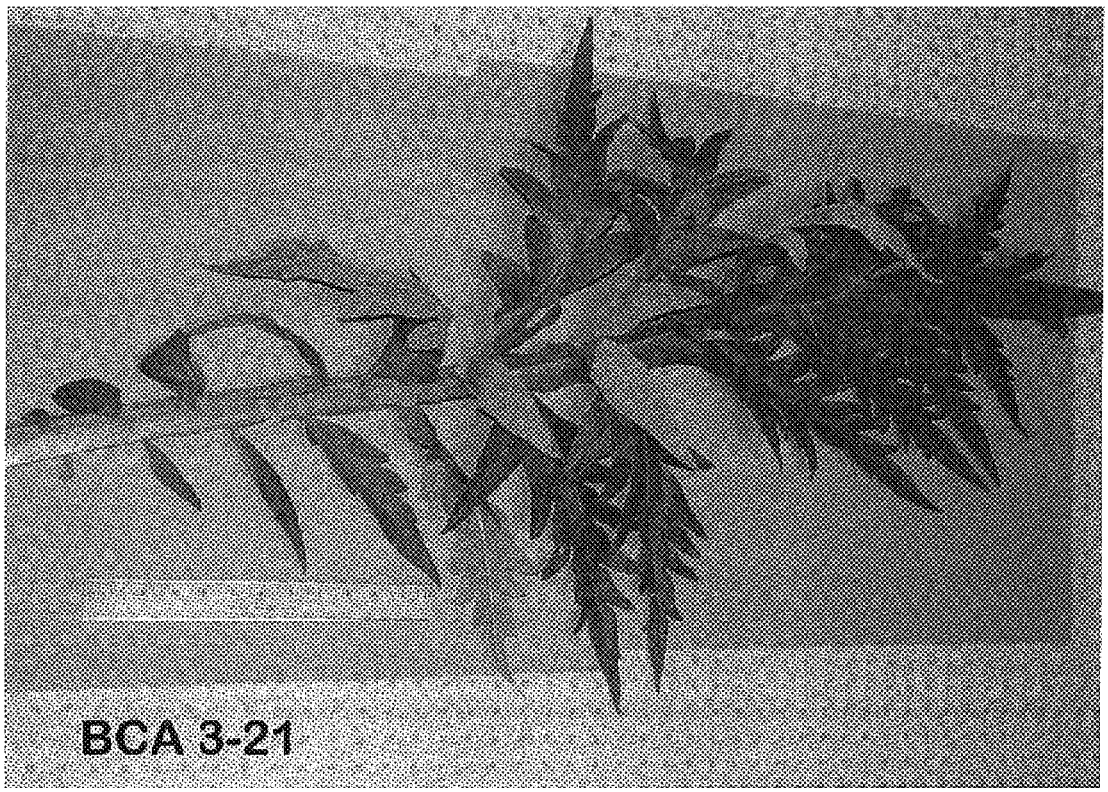
FIG. 2 shows a side elevational view of 'BCA 3-21's' foliage in full color.
Figure 3:
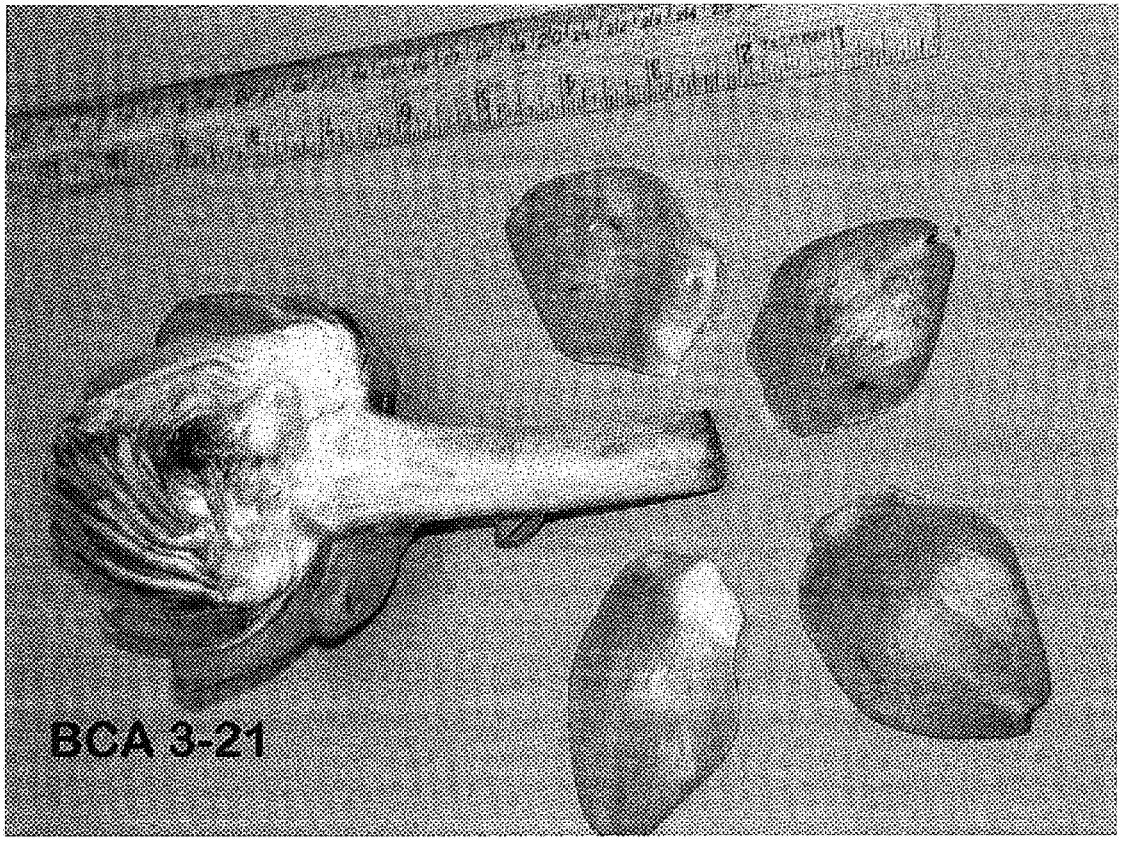
FIG. 3 shows a close-up view of the vertical cross-section of 'BCA 3-21's' fruit in full color.
Figure 4:
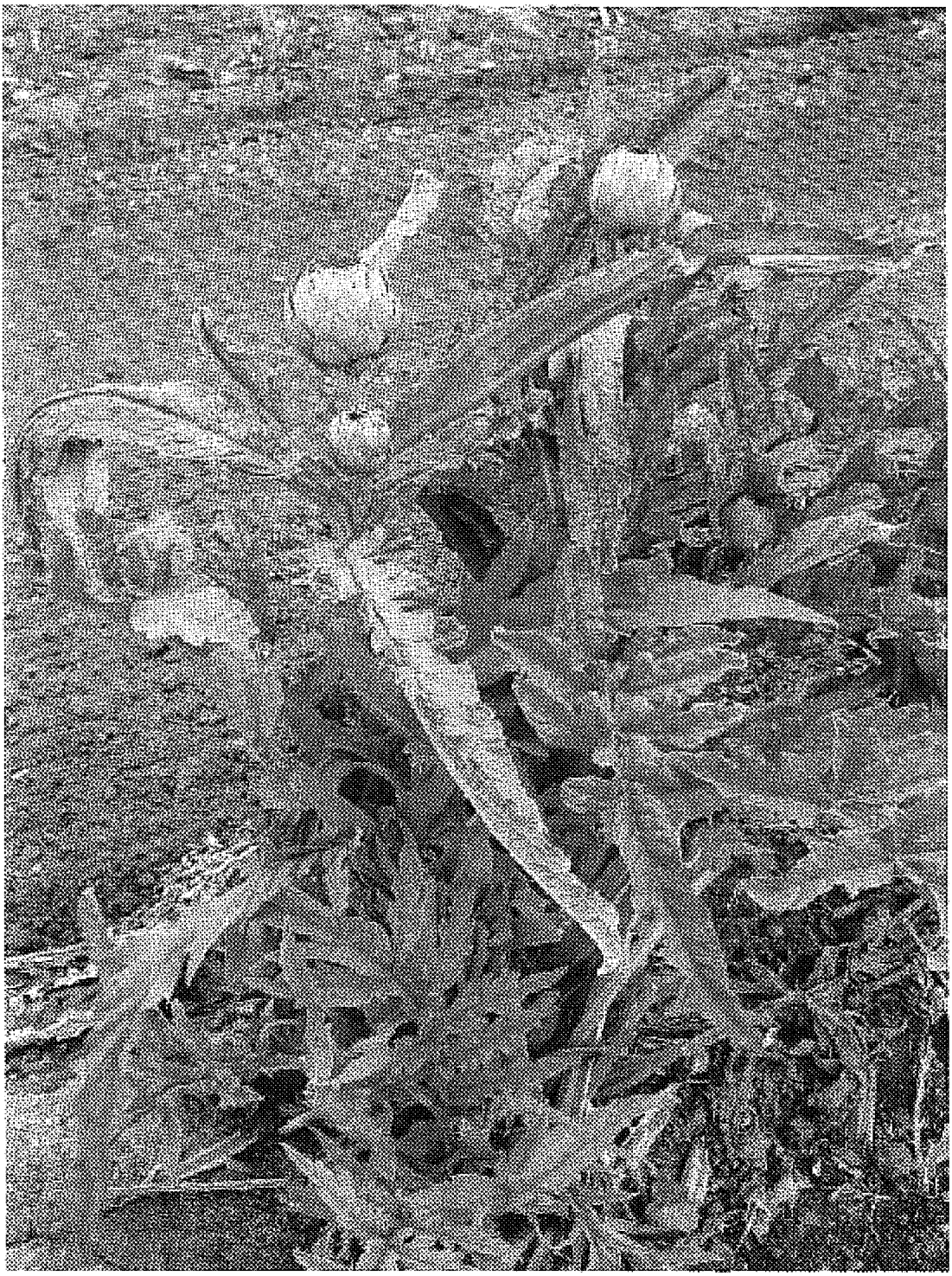
FIG. 4 shows a side elevation view of the 'BCA 3-21' plant in whole.

The following observations, measurements, and values describing the new artichoke plant are based upon observations of plants grown in Lompoc, Calif. The selection varietal was a single plant that was then reproduced. Selection was performed in an outdoor field setting. Unless otherwise indicated, the data were collected from plants that originated from plants that had been grown in Perpignan, acclimatized in California and then vegetatively divided. The plants were grown in the soil in rows where row spacing (bed centers) was at 80 inches, and individual plant spacing at 36 inches. Unless otherwise indicated, the measurements described herein were obtained from plants grown in accordance with the following: after acclimatization, plants were planted in the field in July 2001 and harvested in March of 2002. The plants were cut back and split. New plants were planted in July of 2002 and measurements performed in December of 2002 or January of 2003. Color references are measured against The Royal Horticultural Society Colour Chart.

Plant growth is indicated below as "vigorous". Exemplary growth data showed plant growth to an average of 42 inches in height and 104.5 inches in width in a period from Jul. 8, 2004 to Jan. 26, 2005.

General:

*Parentage.*—Seed parent: 'Camus'. Pollen parent: 'Camus'.

*Classification.*—*Cynara Scolymus* L.

*Propagation.*—Asexual production by division.

Plant:

*Height.*—160.7 to 176.5 cm; average 165.4 cm.

*Width.*—221.0 to 238.8 cm; average 224.0 cm.

*Form.*—Full.

*Growth habit.*—Upright with lateral spread of leaves and shoots.

*Plant vigor.*—Vigorous.

Main stem:

*Diameter.*—6.0 to 8.9 cm; average 7.5 cm.

*Length.*—Approximately 160.7 to 176.5 cm.

*Average internode distance.*—Approximately 7.4 to 12.7 cm; mean 9.0 cm.

Side shoots:

*Number.*—1 to 5 shoots per plant; average 2.6 shoots per plant.

*Development.*—Moderate.

*Length.*—15 to 48 cm; mean 34 cm.

*Diameter.*—1.8 to 3.2 cm; mean 2.8 cm.

*No. of leaves per shoot.*—2 to 7 leaves.

*Average internode distance.*—3.9 to 6.4 cm.

*Color.*—Highly Pubescent; Green group between 144A and 144B.

Capitulum:

*Primary size.*—Approximately 13 cm, slightly smaller than 'Green Globe' (unpatented) at the same maturity.

*Shape.*—Oval.

*Texture.*—Smooth, intermediate hardness.

*Fragrance.*—Very mild.

*Weight.*—200 to 400 gm.

Bract:

*Length.*—Approximately 7 cm.

*Width.*—Approximately 5 cm.

*Shape.*—Ovate, longer than broad, and thick.

*Texture.*—Smooth, intermediate hardness.

*Number.*—Approximately 116 per head.

*Color* (*inner*).—Green Group between 140A and 140B.

*Color* (*outer*).—Green Group between 140B and 140C.

*Firmness.*—Firm and fleshy with thick basal thickness.

*Spinosity.*—None, or minimal — less than 1 mm.

*Basal thickness.*—6 to 17 mm.

Miscellaneous features:

*Heart description.*—Concave full, well developed with thick bract connection, not as concave as 'Green Globe' and slightly broader.

*Receptacle thickness.*—Approximately 1.4 cm.

*Heart color.*—Yellow green group between 145A and 145B.

*Florets.*—Sterile.

*Pappus length.*—Approximately 1.6 cm.

*Pappus color.*—Yellow green group 145D.

*Head firmness.*—Firm, heads are dense and solid.

*Gloss.*—Intermediate; less glossy than 'Green Globe'.

*Cold storage* (*hold quality*).—Good, heads remain firm and free of decay, no browning or blackening of any capitulum tissue, except some browning of the cut and exposed stem.

*Head exterior* (*oxidation*).—Moderate response; some tissue is slightly browned not blackened.

*Head response* (*weather*).—No adverse responses to weather conditions were observed on heads or other plant tissues; more sensitive to freezes than similar varieties.

*Disease.*—Older leaves are susceptible to *Ramularia* leaf spot.

*Bud burst.*—March 10 to March 30.

Foliage:

*Density.*—Dense: many large leaves off main stem with leafy side shoots development as well.

*Leaf shape.*—Long, narrow, slightly oval overall, with multiple lobes such that the outer edges appear coarsely serrated, wherein the apex is acute and the petiole attaches to the center of a slightly obcordate base.

*Width.*—Approximately 65.4 to 76.1 cm.

*Distance between main lobes.*—Approximately 9.8 to 12.7.

*No. of leaves on main stem.*—9 to 22 leaves.

*Leaf ratio.*—Approximately 1.9 to 2.5.

*Leaf area.*—Approximately 4,137 to 5,531 cm sq.

*Upper leaf surface color.*—Green Group 137A to 137B.

*Lower leaf surface color.*—Green Group 139B to 139C.

*Texture.*—Slightly but uniformly textured; glossy with rough intervenal texture.

*Pubescence.*—Sparse, some visible pubescence on lower leaf surface.

*Lobe width.*—Approximately 10.2 to 15.6 cm.

*Lobe indentation.*—Approximately 7.8 to 9.2 cm.

*Petiole length.*—8 to 11.25 cm; average 10.4 cm.

*Petiole width.*—2.5 to 3.8; average 3.6 cm.

*Petiole thickness.*—Approximately 1.0 to 1.9 cm.

*Petiole color.*—Green Group 141C.

*Petiole texture.*—Spindled, wherein multiple ridges, running parallel to the lengthwise orientation, radiate around the petiole.

What is claimed is:

1. The new distinct variety of artichoke plant substantially as shown and described, characterized particularly as to novelty by the characteristics listed above.

* * * * *